(12) United States Patent
Thilly

(10) Patent No.: US 8,720,501 B2
(45) Date of Patent: May 13, 2014

(54) PYRAMID SHAPED NEEDLE POINT

(75) Inventor: Jacques Thilly, Rixensart (BE)

(73) Assignee: Aseptic Technologies S.A., Les Isnes (BE)

( * ) Notice: Subject to any disclaimer, the term of this patent is extended or adjusted under 35 U.S.C. 154(b) by 642 days.

(21) Appl. No.: 12/734,501

(22) PCT Filed: Nov. 6, 2008

(86) PCT No.: PCT/EP2008/065094
§ 371 (c)(1),
(2), (4) Date: Aug. 2, 2010

(87) PCT Pub. No.: WO2009/060047
PCT Pub. Date: May 14, 2009

(65) Prior Publication Data
US 2010/0294796 A1    Nov. 25, 2010

(30) Foreign Application Priority Data

Nov. 6, 2007   (GB) .................................. 0721778.9

(51) Int. Cl.
*B67C 3/04*    (2006.01)
(52) U.S. Cl.
USPC .............................. 141/329; 141/59; 604/411
(58) Field of Classification Search
USPC ............ 141/59, 290, 285, 329, 330; 604/274,
604/411, 403, 414, 6.05; 600/577; 222/80
See application file for complete search history.

(56) References Cited

U.S. PATENT DOCUMENTS 2,711,733 A * 6/1955 Jacoby, Jr. .................... 604/274
3,906,932 A   9/1975 Ayres
4,585,446 A   4/1986 Kempf
(Continued)

FOREIGN PATENT DOCUMENTS

DE    299 01 139 U1    4/1999
GB        829383        3/1960
(Continued)

OTHER PUBLICATIONS

International Search Report for PCT/EP2008/065094 (Feb. 2, 2009).

*Primary Examiner* — Jason K Niesz
(74) *Attorney, Agent, or Firm* — Klarquist Sparkman, LLP

(57) ABSTRACT

A hollow needle comprising a shaft having a distal portion suitable for passing through an elastomer closure of a container, said shaft extending in a longitudinal direction and having a central longitudinal axis, and having an internal longitudinal conduit therein for the flow of liquid and one or more orifices communicating between the conduit and the exterior of the needle, the distal portion of the shaft being provided with a pointed end that has a profile comprising a cutting edge in the form of two part cutting edges converging in the longitudinal direction to meet at the needle point, each part cutting edge extending in a straight line in a widthways direction across a plane including the central longitudinal axis, on both widthways sides of the cutting edge the pointed end having a profile which is a non-cutting surface, wherein the pointed end of the needle tapers from an outer surface of said distal portion toward the point of the needle, and the distance, measured in a further plane defined by said two part cutting edges between the outermost ends of said part cutting edges, is smaller than the largest outer dimension of said distal portion, measured perpendicular to said central axis in said further plane.

12 Claims, 2 Drawing Sheets

(56) References Cited

U.S. PATENT DOCUMENTS 5,466,224 A * 11/1995 Yoon .................... 604/164.12
7,070,583 B1 * 7/2006 Higuchi et al. ............ 604/274
2006/0266431 A1 * 11/2006 Thilly et al. ............... 141/329

FOREIGN PATENT DOCUMENTS

| WO | WO 2004/035119 A1 | 4/2004 |
| WO | WO 2004/064903 A1 | 8/2004 |
| WO | WO 2004/096114 A1 | 11/2004 |

* cited by examiner

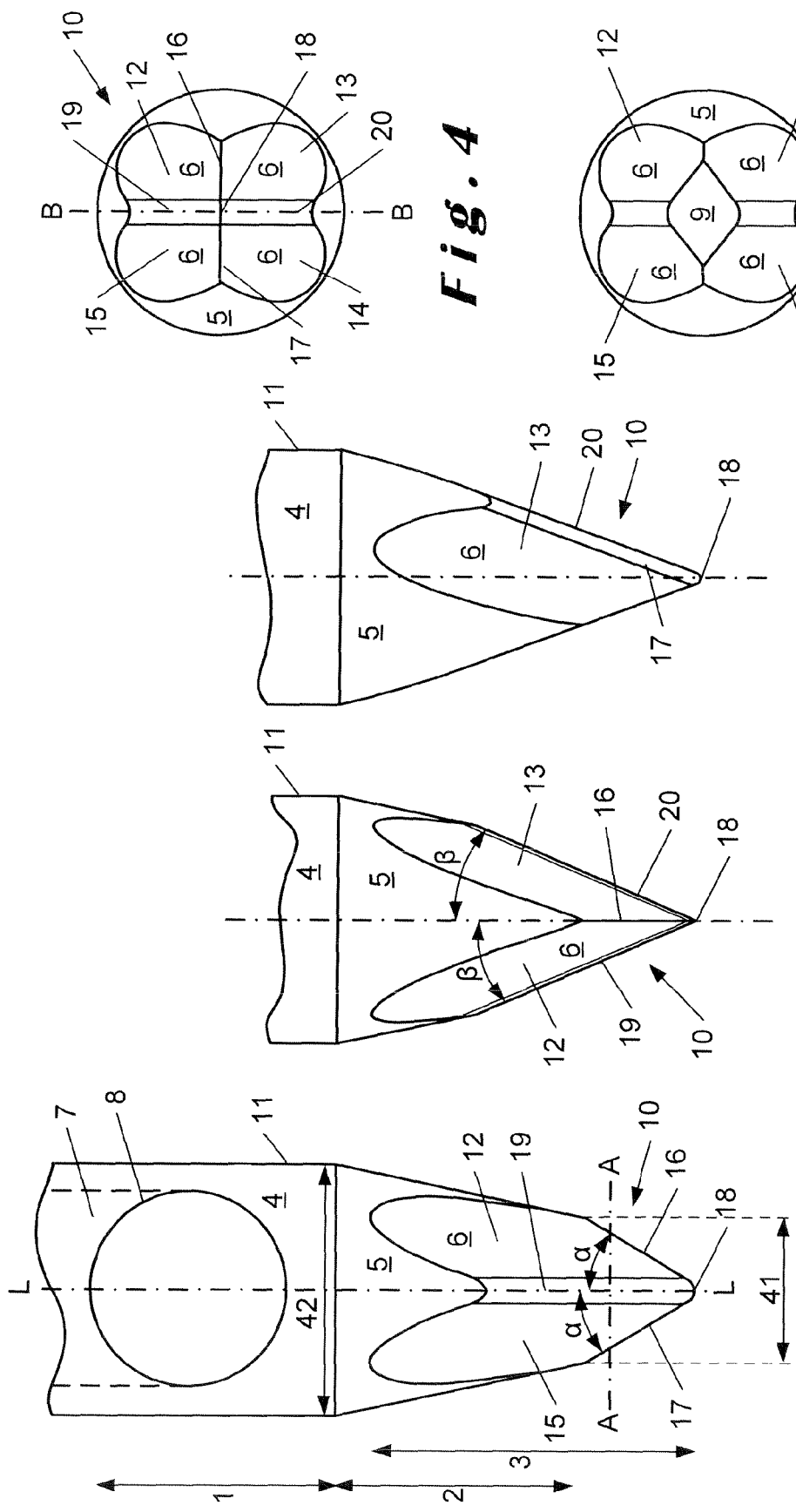

PYRAMID SHAPED NEEDLE POINT

CROSS REFERENCE TO RELATED APPLICATIONS

This is the U.S. National Stage of International application No. PCT/EP2008/065094, filed Nov. 6, 2008, which was published in English under PCT Article 21(2), which in turn claims the benefit of GB No. 0721778.9, filed Nov. 6, 2007, which is incorporated herein by reference in its entirety.

The present invention relates to a hollow needle comprising a shaft having a distal portion suitable for passing through an elastomer closure of a container, said shaft extending in a longitudinal direction and having a central longitudinal axis, and having an internal longitudinal conduit therein for the flow of liquid and one or more orifices communicating between the conduit and the exterior of the needle, the distal portion of the shaft being provided with a pointed end that has a profile comprising a cutting edge in the form of two part cutting edges converging in the longitudinal direction to meet at the needle point, each part cutting edge extending in a straight line in a widthways direction across a plane including the central longitudinal axis, on both widthways sides of the cutting edge the pointed end having a profile which is a non-cutting surface.

Such a needle is known from WO2006/044236. The disclosed needle is intended to withdraw liquid from a container and is not intended to be removed from the container. The shaft portion above the point has a reduced diameter so that a ridge is formed. This ridge enables to insert the needle into the container to such an extent that the orifice is located right next to the closure. In this way the container can be emptied substantially completely.

A drawback of the disclosed needle is that when withdrawing the needle from a container, the closure of the container would tear because the ridge surfaces extend laterally outward relative to the distal portion of the shaft. Therefore this needle is not suitable for being used in a process as disclosed in WO-A-2004/096114, in which a liquid is filled into a closed container with a sterile interior by passing a hollow filling needle through a puncturable part of the wall of the container, passing liquid into the container via a longitudinal conduit within the needle and one or more orifices communicating between the conduit and the outer surface of the needle, then withdrawing the needle from the container, then optionally sealing the residual puncture hole left by the needle, typically using heat sealing to fuse the region of the puncturable part adjacent to the puncture hole. In particular this process is applied to filling liquid into a container having a sterile interior and having its mouth closed with a puncturable elastomer closure.

Numerous needle point profiles have been suggested for being applied in the above-mentioned process. For example U.S. Pat. No. 5,178,628 discloses pyramidal points with four or more sharp cutting edges. EP-A-1 698 318 discloses needles with a chisel shaped point.

WO-A-96/31247, WO-A-98/42181, WO-A-03/071889, U.S. Pat. No. 6,270,484, JP-A-2002/028165 and JP-A-2007/151870 are exemplary of more regular pyramidal points. WO-A-2004/096114 and DE-29901139U are examples of disclosures of conical needle points. WO-A-2006/136062 and WO-A-2007/066772 disclose needles having points with more complex combinations of edges and curved surfaces. U.S. Pat. No. 4,537,593 discloses needles with a knife blade at its pointed end.

It is an object of the present invention to provide a hollow needle that, when it has punctured a closure of a container, leaves a puncture hole which is easy to be sealed subsequently.

To this end a hollow needle according to the invention is characterised in that the pointed end of the needle tapers from an outer surface of said distal portion toward the point of the needle, and the distance, measured in a further plane defined by said two part cutting edges between the outermost ends of said part cutting edges, is smaller than the largest outer dimension of said distal portion, measured perpendicular to said central axis in said further plane.

The pointed end of the needle tapering from the outer surface of the distal portion ensures that no tearing of the container closure occurs in withdrawing the needle from the container because this eliminates the presence of a ridge. When the needle is withdrawn, without tearing the closure, the slit shaped cut has side surfaces which meet together effectively and better than the side surfaces of a random hole formed by a conical pointed needle. The distance between the outermost ends of the cutting edges being smaller than the outer dimensions of the distal portion results in that the length of the slit shaped cut is shorter than the outer dimension of the shaft, and thus smaller than the opening that is to be achieved to enter the needle. When the needle enters the container, the slit shaped cut stretches thereby thus applying a force to the needle. This force proved to be advantageous when withdrawing the needle because residual filling liquid is much more effectively wiped of from the needle. This results in no contamination with residual filling liquid on the outer part of the container and thus no loss of filling liquid. Another advantage of the slit shaped cut being smaller than the opening to be achieved in entering the needle is that a smaller slit has to be sealed subsequently.

The cutting edge extending in a straight line in a widthways direction across a plane including the central longitudinal axis results in a puncture hole in the form of a slit in the elastomer closure of the container. Such a cutting edge results in controlled linear cutting at the start of penetration instead of the random cracking of the elastomer material which can occur with a conical pointed needle. Such a cutting edge is also found to require a lower penetration force than a conical pointed needle, and ca. 25% less force has been achieved.

The two part cutting edges are preferably defined by edge surfaces converging with an angle to the longitudinal axis of 20-80°, preferably 25-40°, for example 30+/−2° (the two part cutting edges consequently enclose twice this angle between them). These angle ranges are selected to facilitate a rapid withdrawal of the needle point from e.g. an elastomer closure of a container. Each part cutting edge preferably extends in a straight line across a longitudinally central axis of the needle. Suitably on either widthways side of the cutting edge the rounded non-cutting surfaces are symmetrical about the cutting edge.

According to a preferred embodiment of the invention, a hollow needle is provided in which the shaft of the needle is cylindrical and the pointed end of the invention has a profile which comprises a four sided pyramid, wherein two opposed edges are part-cutting edges, and the other two opposed edges are rounded non-cutting edges. Suitably the side surfaces of the pyramid are planar. In such a pyramid profiled point suitably the two non cutting edges converge in the longitudinal direction with an angle of 10-40°, preferably 20-30° to the longitudinal axis, for example 25+/−2°. (the two part cutting edges consequently enclose twice this angle between them). This angle of convergence may be the angle between the side surfaces of the part cutting edges.

This four sided pyramid shape is found to have the advantage that when the flow of liquid through the conduit is stopped and the needle is withdrawn from the elastomer closure of a container, the pyramid shape is found to be much more effectively wiped of residual filling liquid by the adjacent sides of the slit shaped puncture hole formed through the closure, than is a conical needle point. High speed photography has seen this surprising effect.

According to another preferred embodiment of the invention, the pointed end of the needle tapers from the cylindrical profile of the shaft toward the point of the needle in two stages, comprising a relatively less steeply tapering region more distant from the point, then a second more steeply tapering region between this less steeply tapering region and the needle point. Preferably the less steeply tapering region is formed by a conical surface and the more steeply tapering region is formed by the four sided pyramid. In the longitudinal direction, there is an overlap area where both the less steeply and the more steeply tapering region are present.

The two stages correspond to the cutting stage and stretching stage in the penetration process. The less steeply tapering region is provided for stretching the closure of the container when a slit has already been made, while the more steeply region is provided for cutting the closure of the container as this more steeply region is provided with the cutting edges. The less steeply tapering region being formed by a conical surface and the more steeply tapering region being formed by the four sided pyramid simplifies the manufacturing process of such a needle because no complex shapes are required. The needle tip in essence is a cone shape tip in which the vertex of the cone is cut away in the shape of a pyramid. The pyramid having a top angle or top angles which are larger than a top angle or corresponding top angles of the cone.

Overall dimensions of the needle may be conventional in the filling needle art. For example the diameter of a cylindrical shaft of the needle may be 2-3 mm. The overall length of the region over which the point of the needle tapers from the cylindrical profile of the shaft to the point may be 3-5 mm.

The needle of the invention is typically made of stainless steel.

The needle of the invention is suitably conventionally provided with a connection at a part distanced from the point by which it may be connected to apparatus to drive the point through the elastomer closure of a container. Such apparatus and connections are well known in the art. The needle of the invention is also suitably conventionally provided with a connection at a part distanced from the point by which it may be connected to a source of a liquid to be introduced into a container such as a container. Such apparatus and connections are well known in the art. Suitably the needle of the invention is also provided with a vent groove in its outer surface via which displaced atmosphere from within a container can vent out when liquid is introduced into the container. Such a vent groove is disclosed in WO-A-2004/096114.

A second aspect of the invention provides a process in which a liquid material is introduced into a container having a sterile interior, having the steps of:

providing a container having a sterile interior and bounded by a wall having a puncturable wall part, passing a needle of the first aspect of this invention through the puncturable wall part to the extent that the orifices are within the container, causing a liquid to flow into the container through the conduit until sufficient liquid has been introduced into the container, withdrawing the needle from the puncturable region.

In this process the container is suitably a container, and the puncturable wall part is suitably an elastomer closure of the container.

In this process, optionally the residual puncture hole left after the needle is withdrawn is sealed by heat fusing the parts of the puncturable wall part adjacent to the puncture hole. Suitably in the case of a puncturable wall part being an elastomer container closure the puncture hole may be heat fused using a focused laser beam.

The invention will now be described in more details with respect to the drawings illustrating some preferred embodiments of the invention. In the drawings:

FIGS. 1-3 show various side views of the pointed end of a needle of this invention;

FIG. 4 shows an end view looking upwards as drawn in FIGS. 1-3;

FIG. 5 shows a cross sectional view cut at line A-A of FIG. 1, looking upwards as drawn in FIGS. 1-3.

In the drawings a same reference number has been allocated to a same or analogous element.

Figure 6A:
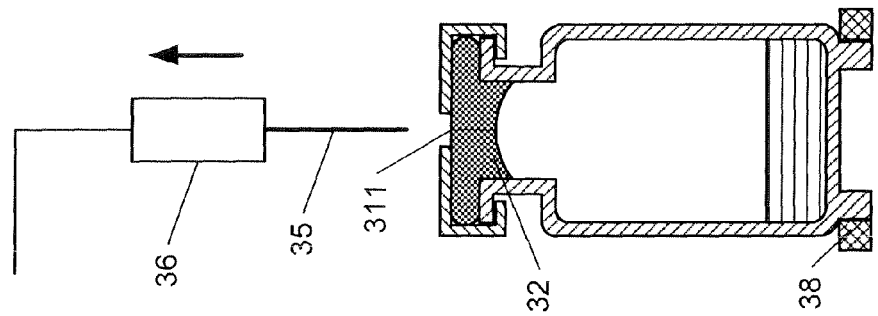
FIG. 6 schematically illustrates a process for filling a container with a liquid using the needle according to the invention.

FIGS. 1-3 show a needle according to the invention, in particular a distal portion of the needle. In this distal portion, three main parts can be seen, the first part 1 is a cylindrical distal portion 4 of the shaft, the second part 2 is a conical part 5 and the third part 3 is a pyramidal part 6. Considering the needle in a direction starting from the shaft towards the needle point, the first, cylindrical part 4, at a distal end of the needle, changes into the second, conical part 5. The second, conical part 5 at its turn changes into the third, pyramidal part 6, which pyramidal part 6 has a tip that forms the point 18 of the needle. Between the second, conical part 5 and the third, pyramidal part 6, in the longitudinal direction, there is an overlap area in which area both the second part 2 and the third part 3 are present, as can be seen in FIGS. 1-3.

The needle is generally of a stainless steel material and suitable for passing through the elastomer closure of a container. The needle itself comprises a cylindrical shaft 11 extending in a longitudinal direction and having a central longitudinal axis L-L.

The first, cylindrical part, also referred to as the shaft 11, has an internal longitudinal conduit 7 therein for the flow of liquid and one or more orifices 8 communicating between the conduit and the exterior of the needle. Such a conduit 7 and orifices 8 are known in the art, e.g. as disclosed in WO-A-2004/096114, or may be otherwise conventional.

As is seen in FIGS. 1-3 the pointed end 10 of the needle tapers from the cylindrical profile of the shaft 11 toward the point 18 of the needle in two stages. These two stages comprising a relatively less steeply tapering region 2 more distant from the point and tapering of an angle of ca. 12° to the longitudinal axis direction, then a second more steeply tapering region 3 between this less steeply tapering region 2 and the point 18.

The relatively less steeply tapering region 2 is formed by the second, conical part 5. The more steeply tapering region 3 is formed by the third, pyramidal part 6. The tip of the pyramidal part 6 forms the point 18 of the needle.

As is seen in FIGS. 1-5 the pointed end 10 has a profile which comprises a pyramid having four planar sides 12, 13, 14, 15. Two edges 16, 17 on opposite sides of the central longitudinal axis L-L are sharp part-cutting edges which converge in the longitudinal direction to meet at the needle point 18. As seen in the view shown in FIG. 4, the two part edges 16, 17 constitute a cutting edge extending in a straight line in a widthways direction across a plane B-B including the central longitudinal axis L-L. The other two opposed edges 19, 20 are rounded edges which would not cut a puncturable material when the pointed end 10 of the needle is driven through a puncturable wall part such as an elastomer container closure.

Because the cutting edges 16, 17 are formed by the edges of the pyramid, and the pyramidal part 6 cuts away the vertex of a cone part 5 of the needle, the cutting edges 16, 17 do not extend to the outermost ends of the shaft, as can be seen in FIG. 1. The distance 41 between the outermost ends of the cutting edges 16, 17, measured in a plane defined by the cutting edges 16, 17, is smaller than the largest outer dimension 42 of the shaft measured in the same plane and perpendicular to the longitudinal axis L-L. This particular feature results, when penetrating a container, in that a slit is formed with a length corresponding to the distance 41 between the outermost ends of the cutting edges. This slit is thus smaller than the width 42 of the object, being the needle, that has is to be entered via this slit. A larger opening will be obtained by stretching the slit so that the needle can enter the container, without thereby tearing the closure of the container. Preferably the length 41 of the slit is smaller than 80%, more preferably smaller than 70%, most preferably smaller than 60% of the largest outer dimension 42 of the distal portion 1 of the shaft measured in the plane defined by the part cutting edges 16, 17 and perpendicular to the longitudinal axis L-L.

To obtain a pyramid having four edges where two opposed edges are cutting edges and other two opposed edges are non-cutting edges, the pyramid preferably has a base in the form of a rhombus 9 as can be seen in FIG. 5. A rhombus 9 has two opposed sharp angles and two opposed obtuse angles which respectively correspond to the cutting and non-cutting edges of the pyramid. Preferably the obtuse angles of the rhombus 9 are rounded so as to obtain a rounded non-cutting edge, as can be seen in FIG. 5. The rounded non-cutting edges 19, 20 preferably have a radius which is larger than 0.1 mm.

As is seen in FIG. 1 the two part cutting edges 16, 17 each converge with an angle α of 30° to the longitudinal axis.

As is seen in FIG. 2 the two non cutting edges 19, 20 converge in the longitudinal direction with an angle β of 25° to the longitudinal axis, forming the angle between the side surfaces of the part cutting edges.

As is seen in FIGS. 1 to 5 the pyramid is symmetrical about the part cutting edges 16, 17.

The non-cutting surfaces each being formed by two planar sides with a rounded-off edge are advantageous in opening the slit without tearing the elastomer closure. FIG. 5 shows the shape 9 in which the slit is spread open and shows that the closure can stretch over the full length of each planar side. If the needle point would have a chisel form, having substantially a cross section in the form of a rectangle as disclosed in EP1698318, the closure would only be able to stretch over the short sides of the rectangle thereby allowing less material to stretch thereby concentrating the stretch into a small area. This would lead to tearing the closure. A pyramidal shaped tip avoids non-uniform stretching of the elastomer material of the closure and thus avoids uncontrolled tearing thereof.

The overall dimensions of the needle 10 are conventional in the filling needle art. The diameter of a cylindrical shaft 11 is 2.4 mm. The overall length of the region 21, 22 over which the point of the needle tapers from the cylindrical profile of the shaft 11 to the point 18 is 3.54 mm.

FIG. 6 schematically illustrates a process for filling a container with a liquid using the needle 10 shown above.

As seen in FIG. 6A a pharmaceutical container 31 is provided having a puncturable elastomer closure 32, held in place in a closing relationship with the mouth of the container 31 by a clamp part 33 which has a central aperture 34 through which the closure 32 is exposed. The interior of container 31 and the part of closure 32 exposed within aperture 34 have been pre-sterilised.

A hollow needle 35 of the type shown and described with reference to FIGS. 1 to 5 is supported above container 32, with its point downwards and aimed at closure 32 through aperture 34. Needle 35 is supported by holder 36 which can be moved reciprocally upwardly and downwardly relative to container 31 by suitable means (not shown). Holder 36 also connects needle 35 to a source (not shown) of a liquid via line 37.

Container 31 has its bottom held by a base 38 which enable container 31 to be held down onto a conveyor (not shown) by which container 31 may be moved underneath needle 35 into the relationship shown.

Figure 6B:
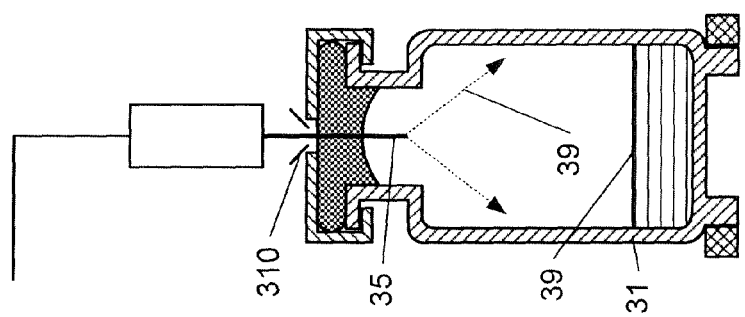

As seen in FIG. 6B, the needle 35 has been moved downwardly by means of a corresponding downward movement of holder 36, so that needle 35 punctures and passes through the closure 32 with orifices shown 15 in FIGS. 1 and 2 within container 31.

Figure 6C:
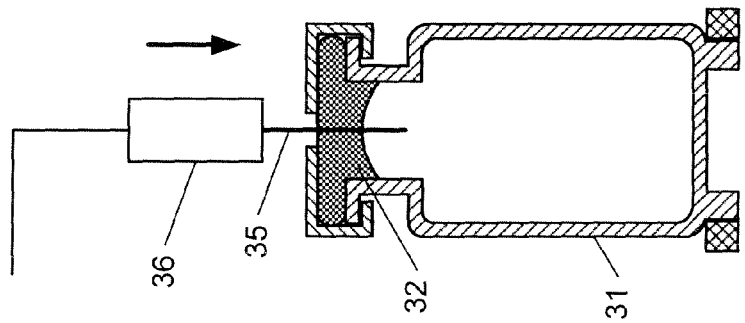

As seen in FIG. 6C, a liquid 39 is caused to flow along line 37 through the internal conduit within the needle 35 (not shown) to exit via orifices (nor shown) in the side of the needle 35 into container 31. The orientation of the orifices directs the liquid 39 to flow out of the needle 35 in a direction having a component parallel to the flow direction, i.e. having a downward component as seen in FIG. 6C. The flow of liquid 39 is seen to be in a direction at a non-zero, non-perpendicular direction to the longitudinal axis of the needle 35. Flowing in this direction the liquid 39 is directed away from the underside of closure 32 and the upper regions of the interior of container 31 toward the bottom of container 31.

A vent groove (not shown) in the outer surface of needle 35 has a length sufficient that when the needle 35 has punctured the closure 32 to its fully intended extent as seen in FIG. 6C one end of the groove 24 is within the container 31 and the other end is exposed outside of the container, so that air within the container 31 can escape via the groove 24 as shown 310.

Figure 6D:
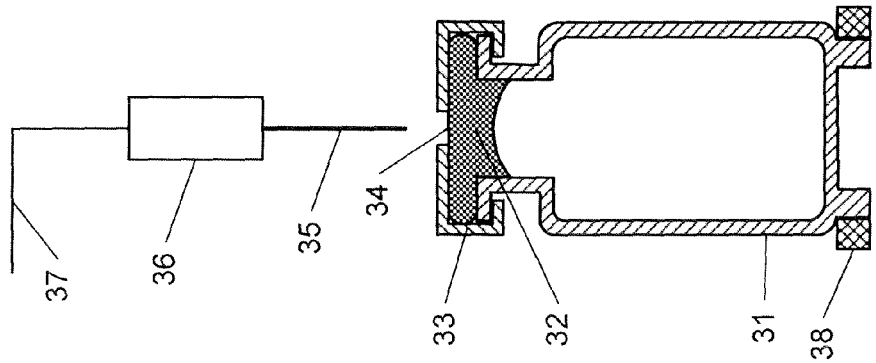

As seen in FIG. 6D a reciprocal upward movement of the is holder 36 and needle 35 has caused the needle 35 to be withdrawn from the container 31 and closure 32. The container 31 may be held down by a holding means (not shown) applied to the base 38. The residual puncture hole 311 may be heat sealed.

The entire operation shown in FIGS. 6A-6D is preferably performed under a downward laminar flow of sterilised air (not shown).

The invention claimed is:

1. A hollow container filling needle comprising a shaft having a distal portion comprising a needle point suitable for passing through an elastomer closure of a container, said needle comprising a vent groove in its outer surface for allowing displaced atmosphere to be vented out of said container when liquid is introduced into said container, said shaft extending in a longitudinal direction and having a central longitudinal axis, and having an internal longitudinal conduit therein for the flow of liquid and one or more orifices communicating between the conduit and the exterior of the needle, wherein considering the needle in a direction along the shaft towards the needle point, the needle comprises a first, cylindrical part, changing into a second, conical part, which at its turn changes into a third, pyramidal part, wherein the needle point has a profile in the pyramidal part comprising a cutting edge in the form of two part cutting edges converging in the longitudinal direction to meet at the needle point, each part cutting edge extending in a straight line in a widthways direction across a plane including the central longitudinal axis, on both widthways sides of the cutting edge the pointed end having a profile which is a non-cutting surface, wherein the pointed end of the needle tapers from an outer surface of said distal portion toward the point of the needle, and the distance, measured in a further plane defined by said two part cutting edges between the outermost ends of said part cutting edges, is smaller than the largest outer dimension of said distal portion at the cylindrical part, measured perpendicular to said central axis in said further plane.

2. The hollow container filling needle of claim 1 wherein the shaft of the needle is cylindrical and the pointed end has a profile which comprises a four sided pyramid, wherein two opposed edges are part-cutting edges, and the other two opposed edges are rounded non-cutting edges.

3. The hollow container filling needle of claim 2, wherein the pointed end of the needle tapers from the cylindrical profile of the shaft toward the point of the needle in two stages, comprising a relatively less steeply tapering region more distant from the point, then a second more steeply tapering region between this less steeply tapering region and the point.

4. The hollow container filling needle of claim 3, wherein the less steeply tapering region is formed by a conical surface and said more steeply tapering region is formed by the four sided pyramid.

5. The hollow container filling needle of claim 4, wherein the pyramid has side surfaces and the side surfaces are planar.

6. The hollow container filling needle of claim 5, wherein the rounded non-cutting edges have a radius which is larger than 0.1mm.

7. The hollow container filling needle of claim 6, wherein the two part cutting edges are defined by edge surfaces converging with an angle to the longitudinal axis of 25-40°.

8. The hollow container filling needle of claim 6, wherein the two non cutting edges converge in the longitudinal direction with an angle of 20-30° to the longitudinal axis.

9. The hollow container filling needle of claim 8, wherein the distance between the outermost ends of the part cutting edges, is smaller than 80% of said outer dimension of the distal portion.

10. The hollow container filling needle of claim 9, wherein the distance between the outermost ends of the part cutting edges, is smaller than 70% of said outer dimension of the distal portion.

11. A process in which a liquid material is introduced into a container having a sterile interior, comprising the steps of:
   providing a container having a sterile interior and bounded by a wall having a puncturable wall part,
   passing the hollow container filling needle of claim 1 through the puncturable wall part to the extent that the orifices are within the container,
   causing a liquid to flow into the container through the conduit until sufficient liquid has been introduced into the container, and
   withdrawing the needle from the puncturable region.

12. The process of claim 11 wherein the container is a container, and the puncturable wall part is an elastomer closure of the container.

\* \* \* \* \*